United States Patent
Chen et al.

(10) Patent No.: US 7,866,202 B2
(45) Date of Patent: Jan. 11, 2011

(54) METHOD OF FABRICATING A CARBON MONOXIDE DETECTOR AND A CARBON MONOXIDE DETECTOR FABRICATED USING THE SAME

(75) Inventors: Ko-Shao Chen, Taipei (TW); Shu-Juan Liao, Taipei (TW); Yun-Huang Chen, Taipei (TW); Jung-Chien Chang, Taoyuan (TW)

(73) Assignee: Forward Electronics Co., Ltd. (TW)

( * ) Notice: Subject to any disclaimer, the term of this patent is extended or adjusted under 35 U.S.C. 154(b) by 377 days.

(21) Appl. No.: 12/153,301

(22) Filed: May 16, 2008

(65) Prior Publication Data

US 2008/0307856 A1    Dec. 18, 2008

(30) Foreign Application Priority Data

May 18, 2007    (TW) .............................. 96117739 A (51) Int. Cl.
*G01N 27/12* (2006.01)
*H01L 21/02* (2006.01)

(52) U.S. Cl. ..................................... 73/31.06; 73/31.02
(58) Field of Classification Search ................. 73/31.01, 73/31.02, 31.05, 31.06
See application file for complete search history.

(56) References Cited

U.S. PATENT DOCUMENTS 4,977,658 A * 12/1990 Awano et al. .............. 29/25.01
6,615,659 B2 * 9/2003 Shibue et al. ............ 73/335.02

OTHER PUBLICATIONS

M. Shoyama and N. Hasimoto, "Effect of poly ethylene glycol addition on the microstructure and sensor characteristics of SnO2 thin films prepared by sol-gel method." Sens. ad Act. B 93 (2003) pp. 585-589.*

* cited by examiner

*Primary Examiner*—Lisa M Caputo
*Assistant Examiner*—Punam Roy
(74) *Attorney, Agent, or Firm*—Bacon & Thomas, PLLC (57) ABSTRACT

Disclosed is a method of fabricating a carbon monoxide detector and a carbon monoxide detector fabricated using the same. Particularly disclosed is a method of fabricating a carbon monoxide detector, which can operate at room temperature and process high detecting selection, and the detector fabricated using the same. The method comprises: providing a substrate having an upper surface; forming two electrode sets on the upper surface of the substrate, and the two electrode sets combined to provide an interdigitated array electrode; forming a tin dioxide layer, which covers the portion of the two electrode sets and the portion of the upper surface; and forming an organic polymer layer on the surface of the tin dioxide layer. The carbon monoxide detector comprises: a substrate having an upper surface; two electrode sets, which are located on the upper surface of the substrate; a tin dioxide layer, which covers the portion of the two electrode sets and the portion of the upper surface; and an organic polymer layer, which is located on the surface of the tin dioxide layer.

21 Claims, 8 Drawing Sheets

METHOD OF FABRICATING A CARBON MONOXIDE DETECTOR AND A CARBON MONOXIDE DETECTOR FABRICATED USING THE SAME

BACKGROUND OF THE INVENTION

1. Field of the Invention

The present invention relates to a method of fabricating a carbon monoxide detector and a carbon monoxide detector fabricated using the same. The present invention particularly relates to a method of fabricating a carbon monoxide detector, which can be provided under room temperature, operated under room temperature, and having optimum sensitizing selectivity.

2. Description of Related Art

In the present surrounding environment, carbon monoxide is often produced as exhaust gas from cars, factory flues, coal, or fuel gas. When an excessive amount of carbon monoxide is inhaled into a human body, it will decrease the oxygen carrying efficiency of hemoglobin. When a human body is exposed to a high concentration of carbon monoxide situation, the cerebrum will lose its normal function and even death may follow. Furthermore, since carbon monoxide possesses the characteristics of lacking color, taste, and stimulus, people cannot detect any danger through their own senses Therefore, the detection technology of the carbon monoxide detector is particularly important in the present living environment.

The present use of carbon monoxide detectors can be classified into the solid semiconductor type, optical type, electrochemical type, and any other types depending on other principles. The solid semiconductor type carbon monoxide detector detects the presence of carbon monoxide by using a metal oxide semiconductor material, such as indium oxide ($In_2O_3$), tin dioxide ($SnO_2$), zinc oxide ($ZnO$), ferric oxide ($Fe_3O_4$), tungstic oxide ($WO_3$), etc. Therefore, when other gases appear in the same space, the detecting ability of these solid semiconductor type carbon monoxide detectors is impaired, and this causes low selectivity and stability, which may be large improved. Besides, these solid semiconductor type carbon monoxide detectors need high operation temperature, such as 200 to 400° C., to be able to work, and all they need high temperature processes for fabrication. Therefore, there are many limits in the providing and using of these solid semiconductor type carbon monoxide detectors.

Figure 1:
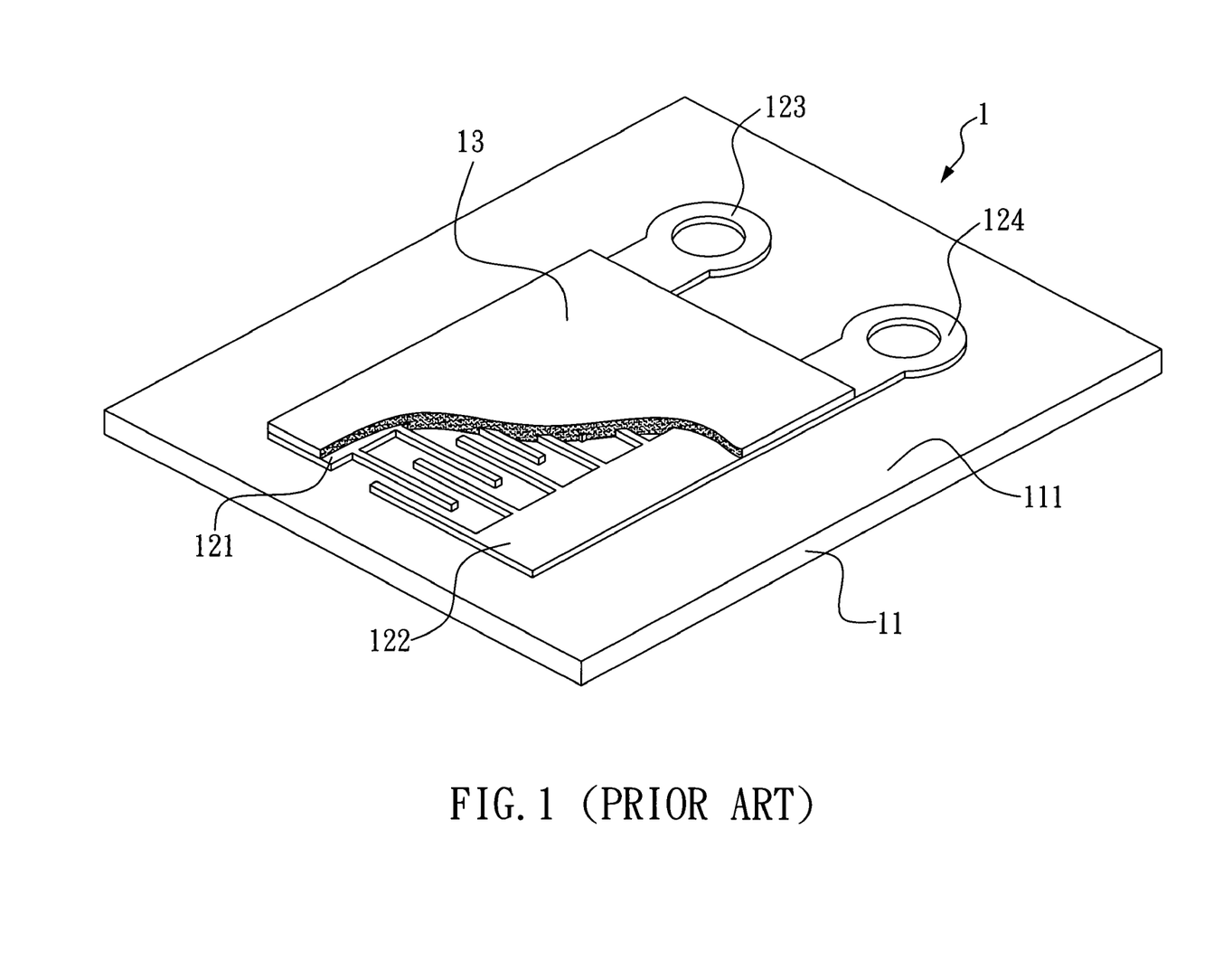
FIG. 1 is a graphic diagram showing the carbon monoxide detector of the prior art.

FIG. 1 illustrates a conventional carbon monoxide detector 1 comprising a substrate 11 having an upper surface 111, which is an aluminum oxide substrate, i.e. a ceramics substrate. A first comb-shaped electrode 121, a second comb-shaped electrode 122, a first pad 123 and a second pad 124 are on the upper surface 111 of substrate 11, wherein the first comb-shaped electrode 121 and the second comb-shaped electrode 122 cross each other in a non-contacting manner, each have one side connecting to the first pad 123 and the second pad 124 respectively, forming two independent electrodes. Furthermore, the first comb-shaped electrode 121 and the second comb-shaped electrode 122 are covered by a tin dioxide layer 13, and the tin dioxide layer 13 is also formed on the upper surface 111 of substrate 11 between the first comb-shaped electrode 121 and the second comb-shaped electrode 122.

Figure 2A:
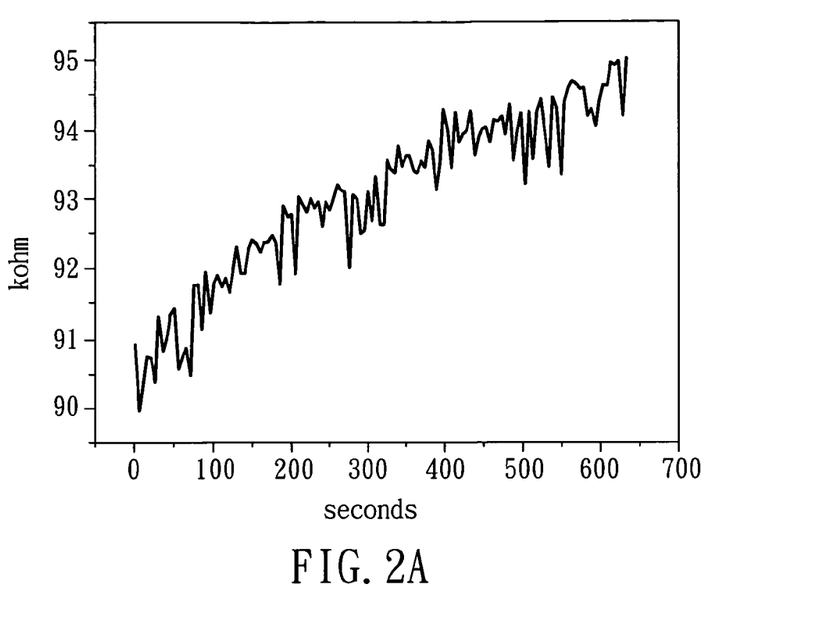
FIGS. 2A and 2B are graphic diagrams showing the resistance testing result when the carbon monoxide detector of the prior art is applied to carbon monoxide detection.
Figure 2B:
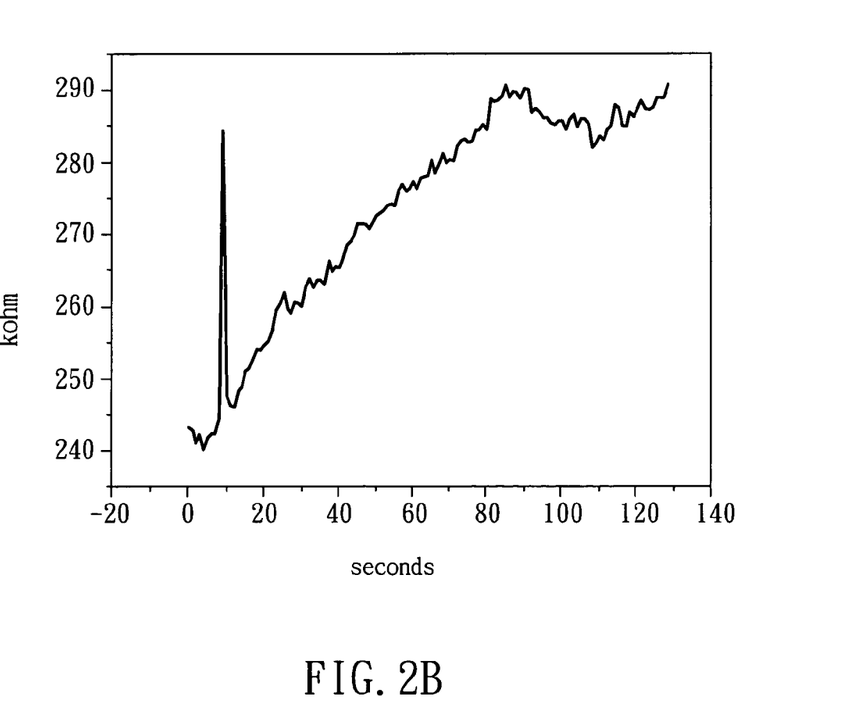

FIG. 2A and FIG. 2B illustrate the resistance measured when a carbon monoxide detector of the prior art is applied in carbon monoxide detecting, the difference is that the vapor pressure of oxygen and tetramethyltin in the reacting chamber (not shown) of plasma-enhanced deposition machine (not shown) is 20 mtorr in FIG. 2A when forming the tin dioxide layer of carbon monoxide detector known in the prior art, and the vapor pressure of oxygen and tetramethyltin in the reacting chamber (not shown) of plasma-enhanced deposition machine (not shown) is 40 mtorr in FIG. 2B when forming the tin dioxide layer of carbon monoxide detector known in the prior art.

As shown in FIG. 2A and FIG. 2B, no matter which kind of carbon monoxide detector of the prior art is placed in a detecting chamber (the carbon monoxide concentration in chamber is 400 ppm), when the resistances are measured, all data obtained are unreliable and the detectors cannot be used to detect carbon monoxide.

Therefore, there is a commercial need for a method to provide a carbon monoxide detector at room temperature, and the carbon monoxide detector (provided using the same) can detect at room temperature and possess higher selectivity.

SUMMARY OF THE INVENTION

A method of fabricating a carbon monoxide detector according to the present invention comprises: providing a substrate having an upper surface; forming two electrode sets on the upper surface of the substrate, and the two electrode sets being combined to provide an interdigitated array electrode; forming a tin dioxide layer, which covers the portion of the two electrode sets and the portion of the upper surface; and forming an organic polymer layer on the surface of the tin dioxide layer.

A carbon monoxide detector according to the present invention comprises: a substrate having an upper surface; two electrode sets, which are located on the upper surface of the substrate, and the two electrode sets combined to provide an interdigitated array electrode; a tin dioxide layer, which covers the portion of the two electrode sets and the portion of the upper surface; and an organic polymer layer, which is located on the surface of the tin dioxide layer.

Therefore, a method of fabricating a carbon monoxide detector comprises forming a tin dioxide layer of the carbon monoxide detector by low temperature plasma-enhanced deposition method, forming another organic polymer layer on tin dioxide layer by spin coating, UV graft polymerization or screen printing. The processes above can be performed at room temperature, therefore the method of fabricating a carbon monoxide detector according to the present invention can provide a carbon monoxide detector at room temperature, and the process can easily and effectively improve the process yield. Furthermore, the carbon monoxide detector provided by the method according to the present invention can detect at room temperature and does not need to be heated to several hundred degrees Celsius in the detection process. Moreover, the carbon monoxide detector provided by the method according to the present invention is not affected by other gases present in the same space and possesses higher detecting selectivity.

To fabricate the carbon monoxide detector of the present invention, any method can be used that forms these two electrode sets (an interdigitated array electrode pair) on the upper surface of the substrate, but preferably is by screen-printing. Any method can be used to form the tin dioxide layer in the method of fabricating the carbon monoxide detector of the present invention, but preferably is by plasma-enhanced deposition method or spin coating to form the tin dioxide layer. In the method of fabricating the carbon monoxide detector of the present invention, the plasma-enhanced deposition method used to form the tin dioxide layer can use plasma of any power, but preferably the power of plasma treatment is set at 25 to 150 W and most preferably is 100 W. In the method of fabricating the carbon monoxide detector of the present invention, the plasma-enhanced deposition method used to form the tin dioxide layer can use any kind of reacting gases, but preferably includes at least oxygen and tetramethyltin. In the method of fabricating the carbon monoxide detector of the present invention, the plasma-enhanced deposition method used to form the tin dioxide layer can use any kind of plasma, but preferably is low-temperature plasma. The method of fabricating the carbon monoxide detector of the present invention can form any kind of organic polymer layer on the surface of the tin dioxide layer, but preferably is forming a polyethylene glycol layer or an acrylamide layer on the surface of the tin dioxide layer.

In the method of fabricating the carbon monoxide detector of the present invention, any method can be used to form the polyethylene glycol layer on the surface of the tin dioxide layer, but preferably is by spin coating. In the method of fabricating the carbon monoxide detector of the present invention, the spin coating used to form the polyethylene glycol layer can use any spin rate, but preferably is between 800 to 1500 rpm, and most preferably is 1000 rpm at the first spinning stage and 1500 rpm at the second spinning stage. In the method of fabricating the carbon monoxide detector of the present invention, the spin coating used to form the polyethylene glycol layer can use a polyethylene glycol solution with any concentration, but preferably is between 1 to 12 wt % and most preferably is between 3 to 10 wt. %. In the method of fabricating the carbon monoxide detector of the present invention, the polyethylene glycol solution used in spin coating to form the polyethylene glycol layer can comprise polyethylene glycol having any molecular weight, the molecular weight of polyethylene glycol in the polyethylene glycol solution is preferably between 200 to 20,000.

The method of fabricating the carbon monoxide detector of the present invention can use any method to form the acrylamide layer on the surface of the tin dioxide layer, but the acrylamide layer is preferably formed on the surface of the tin dioxide layer by UV graft polymerization. In the method of fabricating the carbon monoxide detector of the present invention, the UV graft polymerization used to form the acrylamide layer on the surface of the tin dioxide layer can use UV of any power, but the power of UV treatment preferably is set at 900 to 1110 W and most is preferably 1000 W. In the method of fabricating the carbon monoxide detector of the present invention, the UV graft polymerization used to form the acrylamide layer on the surface of the tin dioxide layer can use acrylamide solution having any concentration, the concentration of the acrylamide solution is preferably between 8 to 12 wt. % and most preferably is 10%.

The carbon monoxide detector of the present invention can have any kind of substrate, preferably an aluminum oxide substrate or a carbon substrate. The two electrode sets (an interdigitated array electrode pair) of the carbon monoxide detector of the present invention can made of any material, but preferably is Au or Ag. The carbon monoxide detector of the present invention can have any kind of two-electrode sets, but preferably is a comb-shaped electrode. The carbon monoxide detector of the present invention can have any kind of organic polymer layer, but preferably is a polyethylene glycol layer or an acrylamide layer. The carbon monoxide detector of the present invention can have the tin dioxide layer with any thickness, but preferably is between 40 to 1400 nm. The carbon monoxide detector of the present invention can have the polyethylene glycol layer with any thickness, but preferably is between 1000 to 1600 nm.

DETAILED DESCRIPTION OF THE PREFERRED EMBODIMENT

Figure 3:
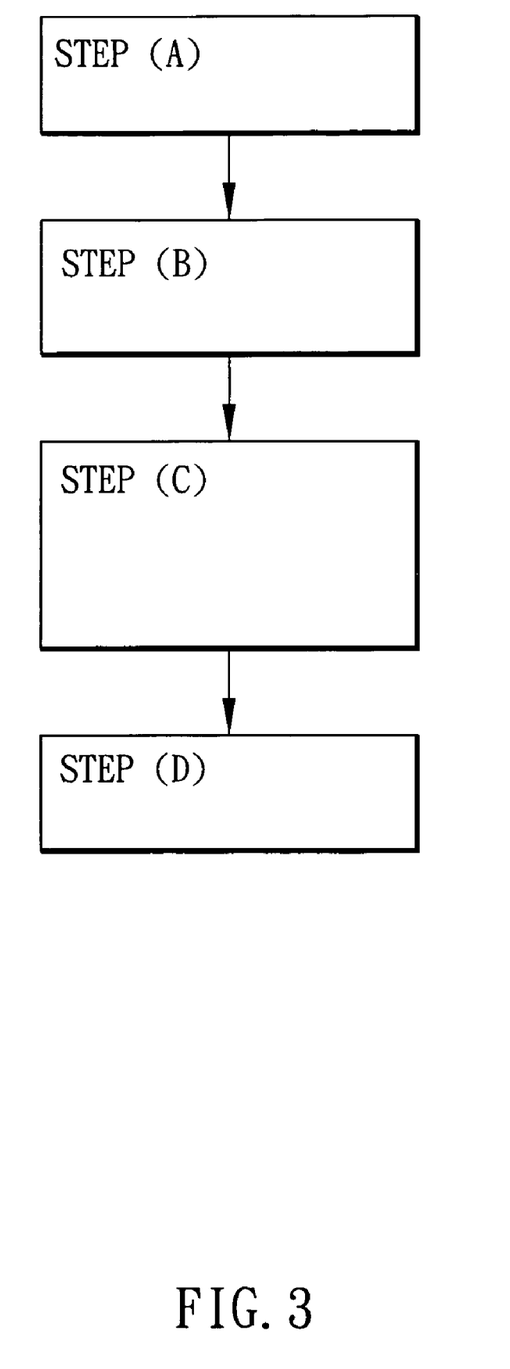
FIG. 3 schematically shows an example of a preparation process according to the first preferred embodiment of the present invention.

The preparation process of a carbon monoxide detector according to the first preferred embodiment of the present invention comprises at least four steps listed below (as shown in FIG. 3):

(A) Providing a substrate having an upper surface; (B) forming two electrode sets on the upper surface of the substrate; (C) forming a tin dioxide layer, which covers the portion of the two electrode sets and the portion of the upper surface; and (D) forming an organic polymer layer on the surface of the tin dioxide layer.

Figure 4:
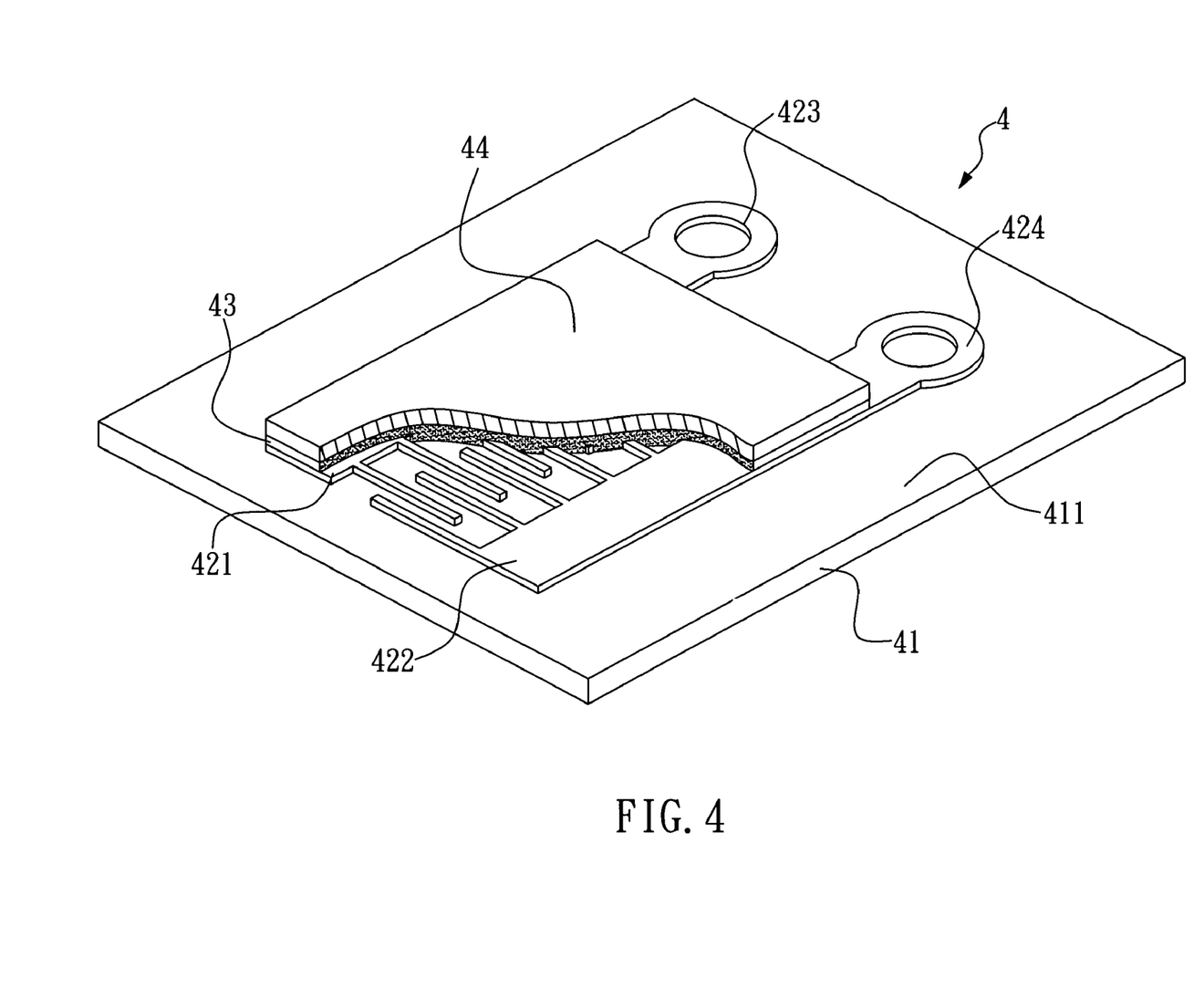
FIG. 4 is a graphic diagram showing the carbon monoxide detector according to the first preferred embodiment of the present invention.

FIG. 4 shown below is a graphic diagram showing the carbon monoxide detector 4 provided by the first preferred embodiment. The method of fabricating the carbon monoxide detector of the first preferred embodiment is detailedly described below:

First, provide a substrate 41 with an upper surface 411. Note that there is no limit on the material of substrate 41. Although substrate 41 is an aluminum oxide ($Al_2O_3$) substrate, i.e. a ceramics substrate, in the present embodiment, it can also be a tin oxide substrate ($SnO_x$). Besides, the shape of the substrate 41 is not limited to the shape in FIG. 4, and it can be any shape according to different application, e.gs. circular or elliptic shape.

Next, form the first comb-shaped electrode 421, the second comb-shaped electrode 422, the first pad 423 and the second pad 424 on the different positions of the upper surface 411 of substrate 41 separately. The first pad 423 and the second pad 424 use a "silver transfer" (mixed previously) printed on the specific position of the upper surface 411 of the substrate 41 by a screen-printing method, then the substrate 41 is provided to a high temperature furnace (not shown) for high temperature sintering process. Both the first comb-shaped electrode 421 and the second comb-shaped electrode 422 use the same screen-printing methods by using another "silver transfer" printed on the specific position of the upper surface 411 of the substrate 41, and then the substrate 41 is provided to a drying furnace (not shown) to proceed drying and baking process. The first comb-shaped electrode 421 and the second comb-shaped electrode 422 together form an interdigitated array electrode. Furthermore, the first comb-shaped electrode 421 and the second comb-shaped electrode 422 are disposed in a crossed yet non-contacting manner, and each have one side respectively connected with the first pad 423 and the second pad 424 to form two independent electrodes.

Then, the substrate 41 is placed into a plasma-enhanced deposition machine (not shown) to provide a tin dioxide layer 43, as shown in FIG. 4. The tin dioxide layer 43 not only covers the first comb-shaped electrode 421 and the second comb-shaped electrode 422, but also deposits on the upper surface 411 of substrate 41 between the first comb-shaped electrode 421 and the second comb-shaped electrode 422. Furthermore, the plasma-enhanced deposition machine (not shown) is filled with various reacting gases comprising oxygen and tetramethyltin into the reacting chamber (not shown) to make both the vapor pressures of oxygen and tetramethyltin reach about 40 Mtorr when using plasma-enhanced deposition method depositing the tin dioxide layer 43. Besides, the whole plasma-enhanced deposition process takes about 10 minutes, and the power of low temperature plasma treatment is set at about 100 W. Once the whole plasma-enhanced deposition process is completed, a tin dioxide layer 43 with a thickness of about 1160 nm will be formed. Preferably, a tin dioxide layer 43 has a thickness about 40 to 1400 nm. It should be noted that the vapor pressures of the various reacting gases comprising oxygen and tetramethyltin in the reacting chamber (not shown) of plasma-enhanced deposition machine (not shown) can be various by the different characteristics of deposited tin dioxide layer 43, and is not limited by 40 mtorr described above. In the second preferred embodiment of the present invention, for example, the vapor pressure of oxygen and tetramethyltin in the reacting chamber (not shown) are both 20 mtorr in the plasma-enhanced deposition process (while forming tin dioxide layer 43).

Finally, a polyethylene glycol layer 44 is formed on the surface of tin dioxide layer 43 by spin coating method, wherein the thickness of polyethylene glycol layer 44 in the present embodiment is preferably 1200 nm. Also, polyethylene glycol layer 44 is not limited to such a thickness, and can possess different kinds of thickness depend on various surroundings applied. Generally, the thickness of polyethylene glycol layer 44 is preferably between 1000 to 1600 nm. When using spin coating to form a polyethylene glycol layer 44 on the surface of the tin dioxide layer 43, the first step is to drop a "polyethylene glycol solution" (prepared previously) on the surface of tin dioxide layer 43, provide the substrate 41 to spin at a spin rate of 1000 rpm for 30 seconds, then spin at a spin rate of 1500 rpm for 20 seconds (it takes 50 seconds for the total spin coating process), then the polyethylene glycol layer 44 is formed on the surface of tin dioxide layer 43. Furthermore, the concentration of the "polyethylene glycol solution" mentioned above is about 3 to 10 wt. % in the present embodiment, and the molecular weight of polyethylene glycol in such "polyethylene glycol solution" is preferably between 200 to 20000. Besides, the concentration and the molecular weight of polyethylene glycol solution will change depending on the different environment applied thereto, but is not limited to the range mentioned above. A carbon monoxide detector 4 shown in FIG. 4 can then be provided by the method of preparing a carbon monoxide detector according to the first preferred embodiment of the present invention when finishing each of the steps described above.

Furthermore, a method of fabricating a carbon monoxide detector of the second preferred embodiment comprise at least 4 steps described below:

(A) providing a substrate with an upper surface; (B) forming two electrode sets on the upper surface of the substrate; (C) forming a tin dioxide layer, which covers the portion of the two electrode sets and the portion of the upper surface; and (D) forming an organic polymer layer on the surface of the tin dioxide layer.

A carbon monoxide detector of the second preferred embodiment is provided by the same method as the first preferred embodiment, except that the vapor pressure of oxygen and tetramethyltin are both 20 mtorr instead of 40 mtorr in the reacting chamber (not shown) of the plasma-enhanced deposition machine (not shown) in step (C) when depositing the tin dioxide layer on the substrate and two electrode sets by plasma-enhanced deposition method. Other operating parameters involved in each step, such as spin rate when forming a polyethylene glycol layer on the surface of the above tin dioxide layer by spin coating, are as the same operating parameters using in The first preferred embodiment for preparing the carbon monoxide detector. Furthermore, the structure and characteristic of the carbon monoxide detector provided by the method of the second preferred embodiment of the present invention will be different from those of the carbon monoxide detector provided by the method of the first preferred embodiment of the present invention.

Figure 5A:
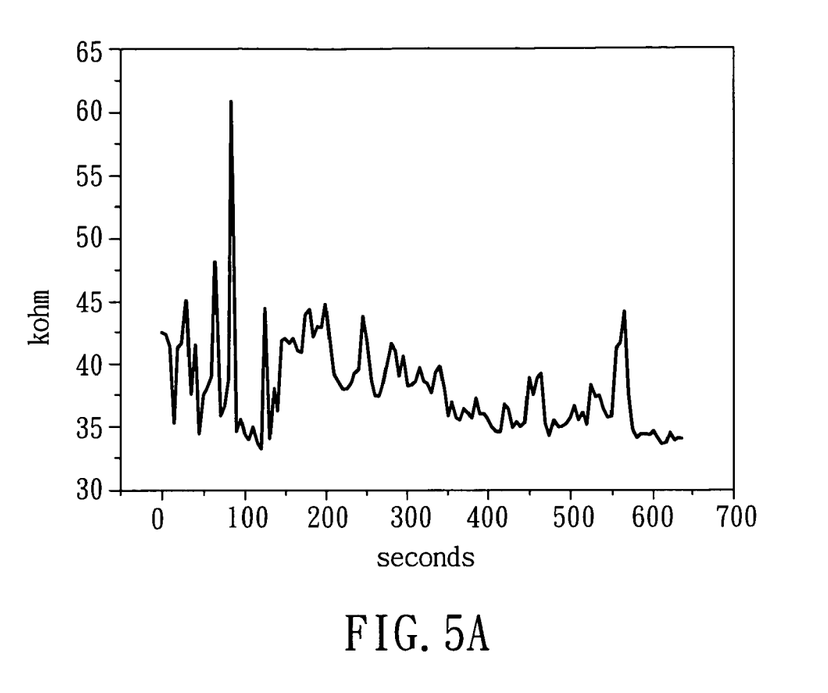
FIGS. 5A and 5B are graphic diagrams showing the resistance testing result when the carbon monoxide detector of the prior art according to two comparative embodiments of the present invention are applied to carbon monoxide detection.
Figure 5B:
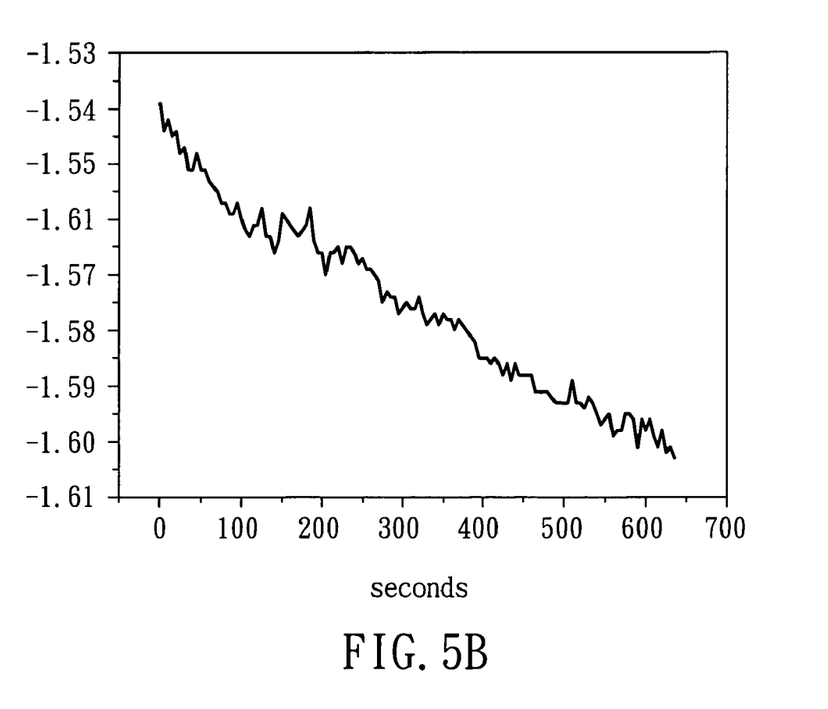

In reference to the graphic diagrams showing the resistance testing result from the carbon monoxide detector from the two comparative embodiments of the present invention, and the graphic from the first preferred embodiment of the present invention into comparison, in which, FIG. 5A and FIG. 5B are graphic diagrams showing the resistance testing result from the carbon monoxide detector of the prior art according to the two comparative embodiments of the present invention when applied to carbon monoxide detection, and the concentration of carbon monoxide in the detecting chamber (not shown) is 400 ppm. Besides, the carbon monoxide detector in FIG. 5A is fabricated by the method comprising the steps below:

First, a substrate having an upper surface is provided, then the first comb-shaped electrode, the second comb-shaped electrode, the first pad and the second pad are formed at respective positions of the upper surface of the substrate. The first pad and the second pad use a "silver transfer" (prepared previously) printed on the specific position of the upper surface of the substrate by screen-printing method, then the substrate is provided to a high temperature furnace for a high temperature sintering process. Both the first comb-shaped electrode and the second comb-shaped electrode use the same screen-printing methods by using another "silver transfer" printed on the specific position of the upper surface of the substrate, and then the substrate is provided to a drying furnace (not shown) to proceed drying and baking processes.

Furthermore, the first comb-shaped electrode and the second comb-shaped electrode are crossed in a non-contact manner, and each has one side respectively connecting with the first pad and the second pad to form two independent electrodes.

The substrate is then placed in a plasma-enhanced deposition machine (not shown) to form a tin dioxide layer. When the tin dioxide layer is deposited by using plasma-enhanced deposition method, oxygen and tetramethyltin-including several gases are filled in the plasma-enhanced deposition machine (not shown) to make both the vapor pressure of oxygen and tetramethyltin reach about 40 mtorr. Besides, the whole plasma-enhanced deposition process takes about 10 minutes, and the power of low temperature plasma treatment was set at about 100 W. Finally, the UV graft polymerization forming a sodium polystyrene sulfonate (NaSS) layer on the surface of the tin dioxide layer is used. Using UV graft polymerization to form a sodium polystyrene sulfonate (NaSS) layer on the surface of the tin dioxide layer is coating "sodium styrene sulfonate solution", prepared previously and the concentration of sodium styrene sulfonate is about 10 wt. %, on the surface of the tin dioxide layer. UV light with 1000 W (and wavelength is most preferably 365 nm) is then used to illuminate on the substrate for 40 minutes, thus a sodium polystyrene sulfonate layer is formed on the surface of the tin dioxide layer by UV-light graft-polymerization.

The method of fabricating the carbon monoxide detector of the prior art in FIG. 5B is the same as FIG. 5A, except that the vapor pressure of oxygen and tetramethyltin are both 20 mtorr instead of 40 mtorr in the reacting chamber (not shown) of the plasma-enhanced deposition machine (not shown) in step (C) when depositing the tin dioxide layer on the substrate and two electrode sets by a plasma-enhanced deposition method. Other operating parameters involved in each step, such as the power of UV when using UV graft polymerization to form a sodium polystyrene sulfonate layer on the surface of the tin dioxide layer, are as the same operating parameters using for preparing the carbon monoxide detector of the prior art in FIG. 5A.

As shown in FIGS. 5A and 5B, during the whole measurement (about 700 seconds), the concentration of carbon monoxide is keep at 400 ppm, the resistance of the monoxide detectors in the two comparative embodiments are out of order, thus cannot show a practicable stable trend at carbon monoxide detection. Therefore, both carbon monoxide detectors from the two comparative embodiments are not capable of carbon monoxide detection. That is, carbon monoxide detectors (from the two comparative embodiments) provided by using UV-light graft-polymerization method of the prior art to form a sodium polystyrene sulfonate layer cannot be used in carbon monoxide detection.

Figure 6A:
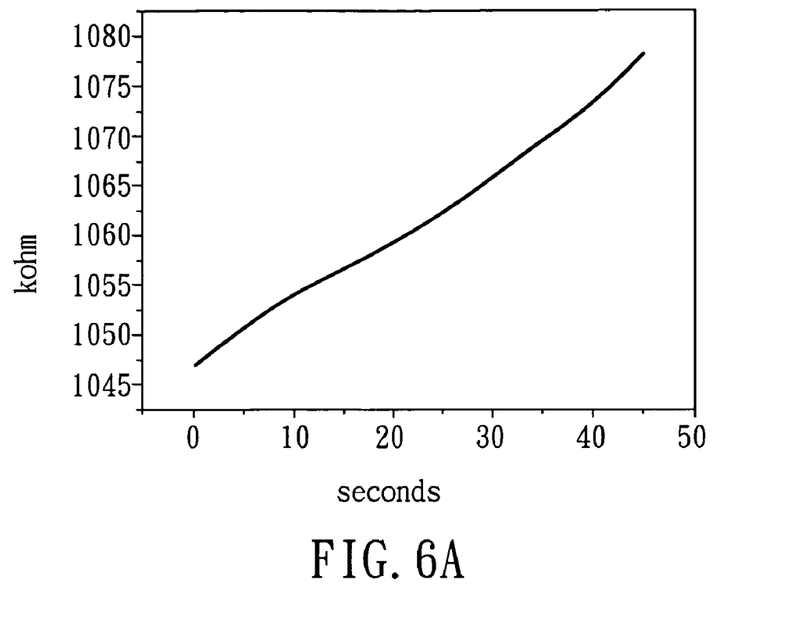
FIG. 6A is a graphic diagram showing the resistance testing result when the carbon monoxide detector according to the first preferred embodiment of the present invention is applied to carbon monoxide detection.

FIG. 6A is a graphic diagram showing the resistance testing result when the carbon monoxide detector according to the first preferred embodiment of the present invention is applied to carbon monoxide detection. As shown in the figure, during the whole measurement (about 700 seconds), the concentration of carbon monoxide is keep at 400 ppm, the resistance of the monoxide detector in the first preferred embodiment shows a steady increasing trend at carbon monoxide detecting that is capable of carbon monoxide detection.

Figure 6B:
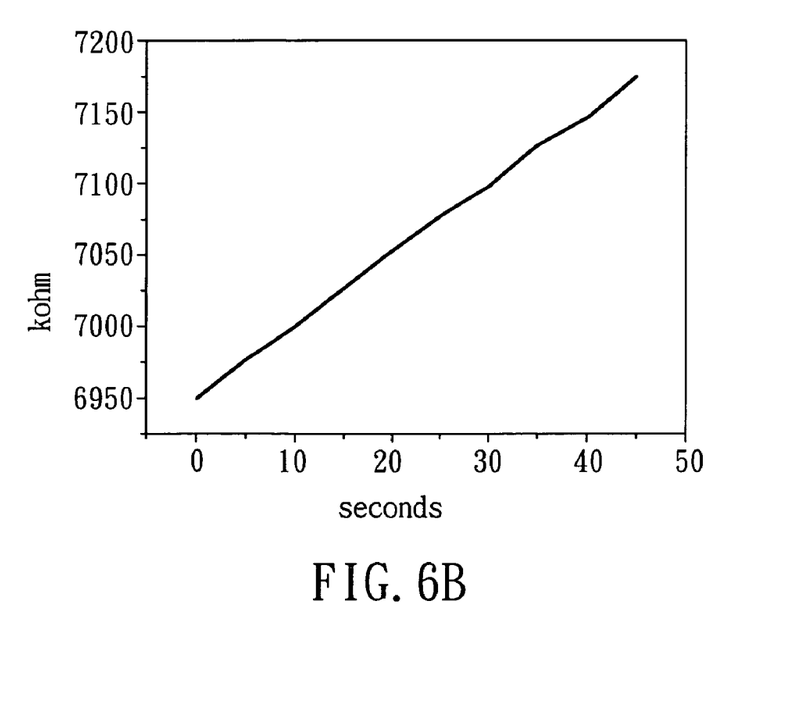
FIG. 6B is a graphic diagram showing the resistance testing result when the carbon monoxide detector according to the second preferred embodiment of the present invention is applied to carbon monoxide detection.

FIG. 6B is a graphic diagram showing the resistance testing result when the carbon monoxide detector according to the second preferred embodiment of the present invention is applied to carbon monoxide detection. As shown in the figure, during the whole measurement (about 700 seconds), the concentration of carbon monoxide is keep at 400 ppm, the resistance of the monoxide detector in the second preferred embodiment shows a steady increasing trend at carbon monoxide detecting that is capable of carbon monoxide detection. Hence both carbon monoxide detectors provided by the method of the first and the second preferred embodiments can be applied to carbon monoxide detecting.

Figure 7:
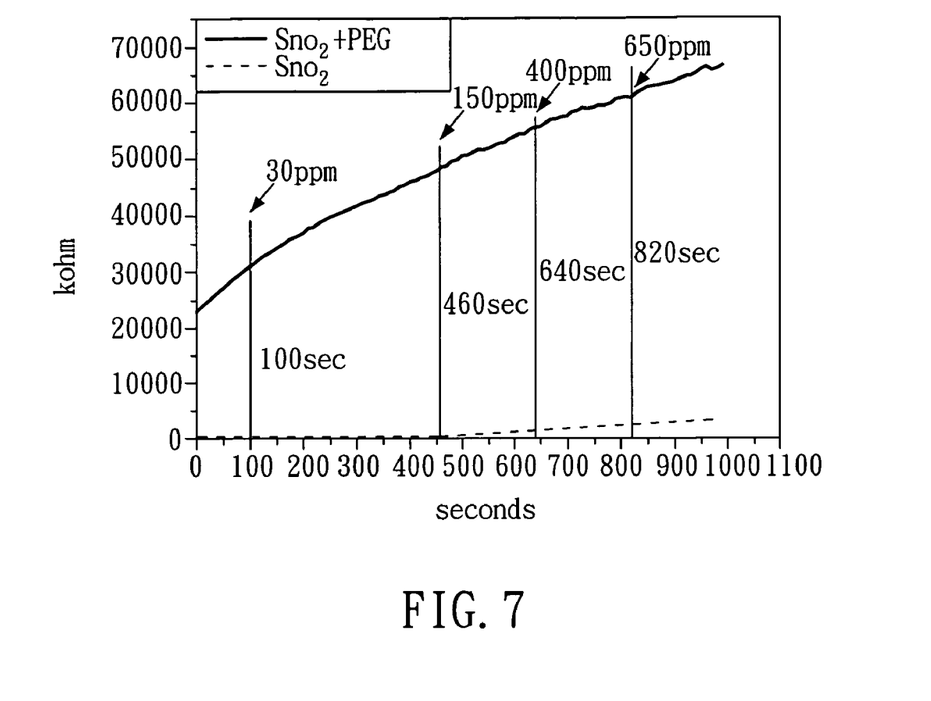
FIG. 7 is a graphic diagram showing the resistance testing result when the carbon monoxide detector according to the first preferred embodiment of the present invention is applied to carbon monoxide detection.

FIG. 7 is a graphic diagram showing the resistance testing result when the carbon monoxide detector according to the first preferred embodiment of the present invention is applied to carbon monoxide detection. The carbon monoxide detector is placed in a detecting chamber (not shown), which is continuously filled with carbon monoxide, then the relativity between resistance of the carbon monoxide detector and concentration of carbon monoxide is measured. As shown in FIG. 7, when continuously filling the detecting chamber (not shown) with carbon monoxide for 100 seconds, the concentration of carbon monoxide in the detecting chamber will reach 30 ppm. As the same, when continuously filling the detecting chamber (not shown) with carbon monoxide for 820 seconds, the concentration of carbon monoxide in the detecting chamber will reach 650 ppm. Therefore, with the increasing time of filling the detecting chamber (not shown) with carbon monoxide, the concentration of carbon monoxide in the detecting chamber (not shown) will increase. Besides, as can be seen in FIG. 7, the resistance of the carbon monoxide detector according to the first preferred embodiment will roughly increase linearly by the concentration of the carbon monoxide of the detecting chamber. Therefore the carbon monoxide detector provided by the method of the first preferred embodiment can be applied to carbon monoxide detecting.

Figure 8:
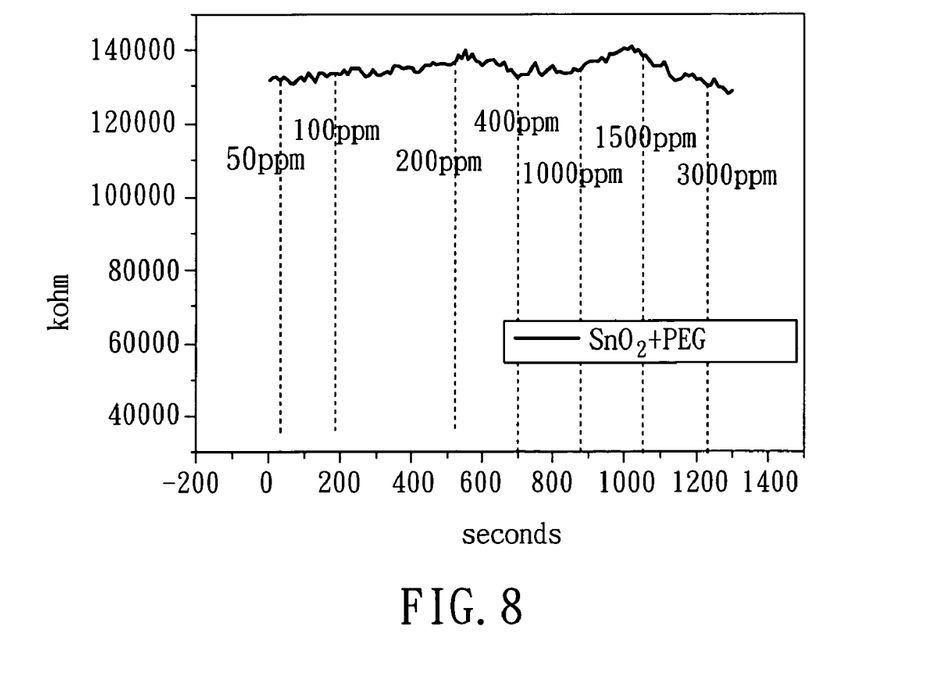
FIG. 8 is a graphic diagram showing the resistance testing result when the carbon monoxide detector according to the first preferred embodiment is applied to methane detection.
Figure 9:
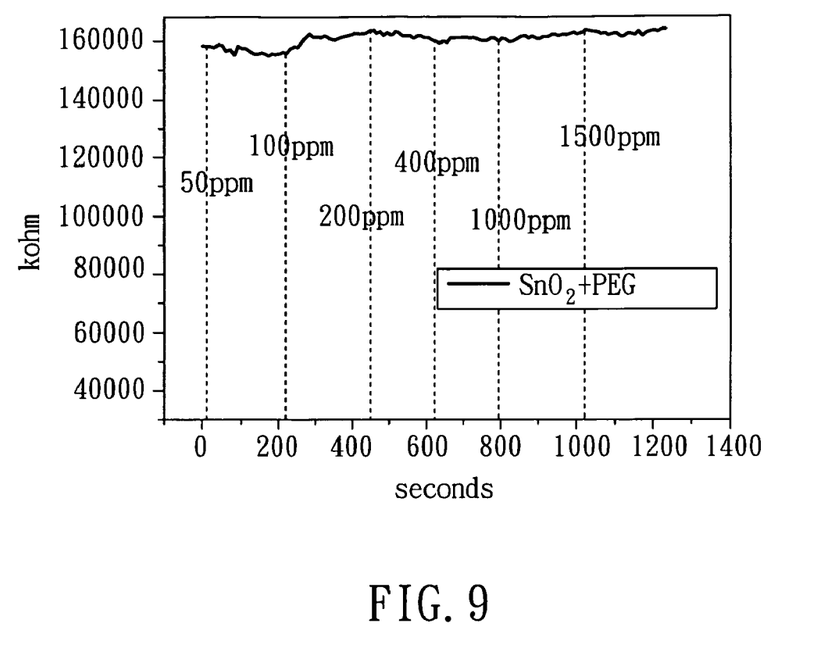
FIG. 9 is a graphic diagram showing the resistance testing result when the carbon monoxide detector according to the first preferred embodiment of the present invention is applied to butane detection.

The carbon monoxide detector according to the first preferred embodiment as shown in FIG. 8 and FIG. 9 will be proved hereinafter that it will not be affected to show any linear increasing or influence to the detecting of target gas (carbon monoxide) of the carbon monoxide detector by the appearance of other gases, as methane and butane, in the surrounding.

As shown in FIG. 8, the graphic diagram showing the resistance testing result when the carbon monoxide detector according to the first preferred embodiment is applied to methane detecting. As shown in the figure, during the whole measurement (about 1400 seconds), no matter the extent of the concentration of methane in a detecting chamber (not shown), the resistance of the carbon monoxide detector according to the first preferred embodiment is roughly the same (steadily over 120000 kohm). Apparently, such a variation in resistance cannot be used in detecting concentration of the gases. Similarly, FIG. 9 is a graphic diagram showing the resistance testing result when the carbon monoxide detector according to the first preferred embodiment of the present invention is applied to butane detection. As shown in the figure, during the whole measurement (about 1400 seconds), the extent of the concentration of butane in a detecting chamber (not shown), the resistance of the carbon monoxide detector according to the first preferred embodiment is roughly the same (steadily over 150000 kohm). As the same, such a variation in resistance cannot be used in detecting concentration of the gases.

Therefore, even other gases, as methane or butane, rather than target gas (carbon monoxide) appear in the detection environment, the linear resistance variation detected by the carbon monoxide detector according to the first preferred embodiment of the present invention is still caused by the concentration change of the target gas (carbon monoxide) during the carbon monoxide detection process. That is, the carbon monoxide detector according to the first preferred embodiment of the present invention has better detecting selectivity.

Figure 10:
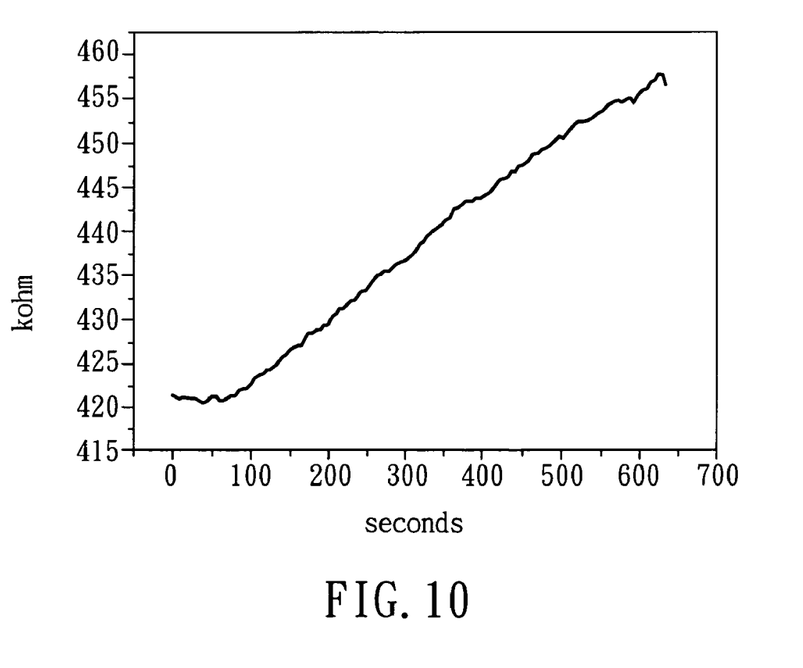
FIG. 10 is a graphic diagram showing the resistance testing result when the carbon monoxide detector according to the third preferred embodiment of the present invention is applied to carbon monoxide detection.

FIG. 10 is a graphic diagram showing the resistance testing result when the carbon monoxide detector according to the third preferred embodiment of the present invention is applied to carbon monoxide detection, the concentration of the carbon monoxide in a detecting chamber (not shown) is 400 ppm when detection has proceeded. Besides, the carbon monoxide detector used in FIG. 10 according to the third preferred embodiment of the present invention is provided by the process steps shown below:

First, providing a substrate having an upper surface, then forming the first comb-shaped electrode, the second comb-shaped electrode, the first pad and the second pad on the different positions of the upper surface of the substrate. The first pad and the second pad use a "silver transfer" (mixed previously) printed on the specific position of the upper surface of the substrate by screen-printing method, then the substrate is provided to a high temperature furnace for a high temperature sintering process. Both the first comb-shaped electrode and the second comb-shaped electrode use the same screen-printing methods by using another "silver transfer" printed on the specific position of the upper surface of the substrate, and then the substrate is provided to a drying furnace (not shown) to proceed drying and baking processes. Furthermore, the first comb-shaped electrode and the second comb-shaped electrode are crossed in a non-contacting manner, and both have one side respectively connecting with the first pad and the second pad to form two independent electrodes.

The substrate is then placed in a plasma-enhanced deposition machine (not shown) to form a tin dioxide layer. When the tin dioxide layer is deposited by using a plasma-enhanced deposition method, oxygen and tetramethyltin-included several gases are filled in the plasma-enhanced deposition machine (not shown) to make both the vapor pressure of oxygen and tetramethyltin reach about 20 mtorr. Besides, the whole plasma-enhanced deposition process takes about 10 minutes, and the power of low temperature plasma treatment was set at about 100 W. Finally, UV graft polymerization is used forming an acrylamide layer on the surface of the tin dioxide layer. Using UV graft polymerization to form an acrylamide layer on the surface of the tin dioxide layer is coating "acrylamide solution", prepared previously and the concentration of acrylamide is about 10 wt. %, on the surface of the tin dioxide layer. UV light with 1000 W is then used to illuminate on the substrate for 40 minutes, thus an acrylamide layer is formed on the surface of the tin dioxide layer by UV-light graft-polymerization.

As shown in FIG. 10, during the whole measurement (about 700 seconds), the concentration of carbon monoxide is kept at 400 ppm, the resistance of the monoxide detector according to the third preferred embodiment shows a steady increasing trend at carbon monoxide detecting. Though the increasing trend is not as steady as in FIGS. 6A and 6B, it is enough for the use in carbon monoxide detection.

To conclude, the carbon monoxide detector according to the present invention forms a tin dioxide layer of a carbon monoxide detector by low temperature plasma-enhanced deposition method, then another organic polymer layer is formed on the tin dioxide layer by spin-coating, UV graft polymerization or screen-printing methods. Those above processes all can be carried out at room temperature, thus the method of fabricating the carbon monoxide detector according to the present invention can fabricate the carbon monoxide detector at room temperature, and the processes of the method are very simple, so as to raise the producing yield effectively. Furthermore, the carbon monoxide detector fabricated by the method according to the present invention can detect at room temperature and does not need to be heated to several hundred degrees for detection. Moreover, the carbon monoxide detector provided by the method according to the present invention is not affected by other gases present in the same space and possesses higher detecting selectivity.

While the present invention has been shown and described in connection with the exemplary embodiments, it will be apparent to those skilled in the art that modifications and variations can be made without departing from the spirit and scope of the invention as defined by the appended claims.

What is claimed is:

1. A method of fabricating a carbon monoxide detector, comprising the steps of:
   providing a substrate having an upper surface;
   forming two electrode sets on the upper surface of the substrate;
   forming a tin dioxide layer, wherein the tin dioxide layer covers the portion of the two electrode sets and the portion of the upper surface; and
   forming an organic polymer layer on the surface of the tin dioxide layer;
   wherein the organic polymer layer is a polyethylene glycol layer provided by spin coating or an acrylamide layer formed by UV graft polymerization.

2. The method according to claim 1, wherein the two electrode sets are formed by a screen-printing method.

3. The method according to claim 1, wherein the tin dioxide layer is formed by plasma-enhanced deposition method.

4. The method according to claim 3, wherein the power of plasma treatment was set at 25 to 150 W in the plasma-enhanced deposition method.

5. The method according to claim 3, wherein the gas applied in plasma-enhanced deposition method at least comprises oxygen and tetramethyltin.

6. The method according to claim 3, wherein low temperature plasma is used in the plasma-enhanced deposition method.

7. The method according to claim 1, wherein the organic polymer layer is a polyethylene glycol layer provided by spin coating.

8. The method according to claim 7, wherein the spin rate during spin coating is 800 to 1500 rpm.

9. The method according to claim 7, wherein a polyethylene glycol solution is used in the spin coating, and the concentration of the polyethylene glycol solution is 1 to 12 wt. %.

10. The method according to claim 9, wherein the polyethylene glycol in polyethylene glycol solution has a molecular weight between 200 to 20,000.

11. The method according to claim 1, wherein the organic polymer layer is the acrylamide layer formed by UV graft polymerization.

12. The method according to claim 11, wherein the power of UV treatment is 900 to 1100 W during UV graft polymerization.

13. The method according to claim 11, wherein an acrylamide solution, which has a concentration between 8 to 12 wt. %, is used in the UV graft polymerization.

14. A carbon monoxide detector comprising:
   a substrate having an upper surface;
   two electrode sets, which are located on the upper surface of the substrate;
   a tin dioxide layer, which covers the portion of the two electrode sets and the portion of the upper surface; and
   an organic polymer layer, which is located on the surface of the tin dioxide layer;

wherein the organic polymer layer is a polyethylene glycol layer provided by spin coating or an acrylamide layer formed by UV graft polymerization.

15. The carbon monoxide according to claim 14, wherein the substrate is an aluminum oxide substrate or carbon substrate.

16. The carbon monoxide detector according to claim 14, wherein the material of two electrode sets is gold.

17. The carbon monoxide detector according to claim 14, wherein the two electrode sets are comb-shaped electrodes.

18. The carbon monoxide detector according to claim 14, wherein the tin dioxide layer has a thickness of 40 to 1400 nm.

19. The carbon monoxide detector according to claim 14, wherein the organic polymer layer is polyethylene glycol layer.

20. The carbon monoxide detector according to claim 19, wherein the polyethylene glycol layer has a thickness between 1000 to 1600 nm.

21. The carbon monoxide detector according to claim 14, wherein the organic polymer layer is acrylamide layer.

* * * * *